United States Patent [19]

Weingaertner et al.

[11] Patent Number: 5,012,034

[45] Date of Patent: * Apr. 30, 1991

[54] PROCESS FOR SEPARATING STYRENE FROM STYRENE-CONTAINING HYDROCARBON STREAMS

[75] Inventors: David A. Weingaertner, Houston; Lynn H. Slaugh, Cypress, both of Tex.

[73] Assignee: Shell Oil Company, Houston, Tex.

[*] Notice: The portion of the term of this patent subsequent to Aug. 7, 2007 has been disclaimed.

[21] Appl. No.: 390,007

[22] Filed: Aug. 7, 1989

[51] Int. Cl.$^5$ ................................. C07C 7/00
[52] U.S. Cl. ........................ 585/806; 585/804; 585/805; 585/807; 585/833; 585/864; 585/867
[58] Field of Search .............. 585/805, 806, 807, 833, 585/864, 867, 804

[56] References Cited

U.S. PATENT DOCUMENTS

| | | | |
|---|---|---|---|
| 2,377,221 | 5/1945 | Francis et al. | 585/807 X |
| 2,406,645 | 8/1946 | Thomas | 585/425 X |
| 3,534,116 | 10/1970 | Fuller | 585/867 X |
| 4,129,605 | 12/1978 | Tabler et al. | 585/806 X |

*Primary Examiner*—Curtis R. Davis
*Assistant Examiner*—William C. Diemler

[57] ABSTRACT

This invention relates to a process for extracting styrene from a styrene-containing hydrocarbon feedstock by:

(a) reacting the feedstock with an anthracene at a temperature ranging of from about 175° to about 275° C. to form a styrene adduct with anthracene,
(b) separating the adduct from the feedstock,
(c) heating the separated adduct at a temperature of from between about 250° to about 450° C. to produce anthracene and styrene, and
(d) individually separating styrene and anthracene from the mixture formed in step (c).

11 Claims, No Drawings

PROCESS FOR SEPARATING STYRENE FROM STYRENE-CONTAINING HYDROCARBON STREAMS

FIELD OF THE INVENTION

This invention relates to a process for separating styrene from hydrocarbon process streams containing styrene, particularly from streams additionally containing ethylbenzene and/or xylenes.

BACKGROUND OF THE INVENTION

Certain pyrolysis liquids available from olefin pyrolysis units contain considerable styrene. At the moment, the styrene is of fuel value only, due to the difficulty in separating the styrene monomer from the copresent ethylbenzene and xylenes. Unfortunately the boiling points of styrene, ethylbenzene and xylenes are very close and conventional distillation techniques are not readily applicable. A method for extracting the styrene from these pyrolysis liquid streams would be of considerable economic importance. Applicants have discovered a method for separating styrene from these pyrolysis streams utilizing an anthracene as a separating agent.

Copending Applications Serial No. 263,218 and Serial No. 263,225, both filed Oct. 27, 1898, disclose the use of an anthracene to separate alpha olefins from internal olefins.

U.S. Pat. No. 3,052,737, issued Sep. 4, 1962, discloses reacting anthracene with vinylcyclohexene to produce an adduct which is then hydrogenated to convert the cyclohexene ring to a cyclohexane ring, followed by pyrolysis to produce vinylcyclohexane and anthracene. This reference does not suggest that anthracene would be useful in separating styrene from ethylbenzene and xylenes.

SUMMARY OF THE INVENTION

This invention relates to a process for extracting styrene from a styrene-containing hydrocarbon feedstock which comprises:

(a) contacting or mixing said feedstock with an anthracene at a temperature ranging of from about 175 to about 275° C. to form an styrene adduct with anthracene, (b) separating said adduct from the feedstock, (c) heating said separated adduct at a temperature of from between about 250 to about 450° C. to produce a mixture containing anthracene and styrene and (d) invidually separating styrene and anthracene from the mixture formed in step (c).

The instant process is particularly suitable when the feedstock contains ethylbenzene and xylenes in addition to the styrene.

DETAILED DESCRIPTION OF THE INVENTION

The hydrocarbon feedstocks preferably used in the process of the instant invention are produced by the pyrolysis of hydrocarbon feedstocks, particularly the pyrolysis of alkanes to produce alkenes (olefin pyrolysis). These feedstocks typically contain aliphatic or nonaromatic-containing olefins and aromatics such as styrene, benzene, toluene, ethylbenzene, xylenes, etc. The feedstocks directly from a pyrolysis unit may be processed according to the instant invention. However, these pyrolysis feedstocks are typically preprocessed before the application of the instant invention in order to remove light ends (e.g., $C_6$ and lighter), heavy ends (e.g., $C_{10}$ and heavier) as well as a substantial portion of the aliphatic olefins, say by distillation. After this preprocessing, the styrene-containing bottoms stream is conveniently processed according to the instant invention in order to extract the styrene. The instant invention is not, however, limited in application to pyrolysis derived streams. It may be applied to any hydrocarbon stream containing styrene. This stream may be, for example, a by-product stream from a conventional ethylbenzene/styrene dehydrogenation unit or a styrene monomer/propylene oxide unit or a polystyrene production unit.

Anthracene is utilized in the instant process to form the adduct primarily with the styrene in the feedstock. As used herein "anthracene" refers to $C_{14}H_{10}$ (molecular weight 178.15) as well as substitued anthracenes possessing similar adducting properties as the unsubstituted anthracene including but not limited to anthracene bearing one, two or more simple substituents, including but not limited to, lower alkyl, e.g., methyl, ethyl, butyl; halo, e.g., chloro, bromo, fluoro; nitro., sulfato; sulfonyloxy., carboxyl, carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituents utilized should be inert under the reaction conditions and relatively small, such that they do not provide so much steric hinderance that the Diels-Alder reaction is inhibited. Suitable substituted anthracenes can be determined by routine experimentation.

The process of the instant invention is basically a four step process wherein (a) anthracene is reacted with the styrene in a feedstock to form an adduct, (b) the adduct is separated from the unreacted feedstock, (c) the adduct is pyrolyzed to release the styrene and regenerate the anthracene, and (d) the styrene and anthracene produced in step c) are independently separated. When other olefins, such as aliphatic olefins such as ethylene, propylene, butylenes, etc., are present in the reacting feedstock, the anthracene will react with any olefins contained therein, and preferably with the alpha olefins, as well as with the styrene. In the later case a fifth step is added to the instant process, that of separating the olefins from the styrene. The olefins can be separated from the styrene by conventional methods, such as distillation.

The Diels-Alder adduct forming reaction is carried out in a conventional fashion. It may be carried out continuously in a stirred tank reactor wherein styrene-containing feedstock and anthracene are added continuously to a stirred tank and a reaction product is continuously withdrawn from the stirred tank. Alternatively, the reaction may be carried out in a batch reactor, wherein the styrene-containing feedstock and the anthracene are charged to an autoclave which is then heated to reaction temperature to complete the reaction. The reaction is typically carried out over a range of temperatures from about 175 to about 275° C., preferably from about 200 to about 250° C., and most preferably from about 210 to about 240° C. Pressures are not critical and typically run from about atmospheric to about 100 atmospheres. The reaction can be carried out in the gas phase or liquid phase or mixed gas-liquid phase. The resultant reaction mixture will contain unreacted feedstock, unreacted anthracene (if the anthracene was in excess) and adduct.

Stoichiometric proportions or an excess of either styrene or anthracene can be used in forming the adducts but an excess of anthracene is preferred. Advantageous ratios of about 1 to 10, preferably about 1 to about 5, and more preferably about 1 to about 2 moles of the anthracene to styrene are utilized. The presence of olefins in the feedstock will call for additional anthracene.

An inert solvent can be utilized to dissolve the feedstock or the anthracene or both in the reactor. Preferred solvents are the hydrocarbon solvents which are liquid at reaction temperatures and in which the styrene-containing feedstock, anthracene and styrene-anthracene adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, xylenes, and the like. The amount of solvent to be employed can vary over a wide range without a deleterious effect on the reaction. The use of a solvent does introduce extra expenses and hence, it is preferable to operate in a solvent-free mode.

After the styrene-anthracene adduct has been formed, it is separated from the reaction mixture. The styrene-anthracene adduct is separated from the reaction mixture by conventional means. For example, it may be separated by flash distillation of the reaction mixture to leave the adduct. Alternatively, it may be separated by cooling the reaction mixture until the adduct crystallizes out, followed by filtration or centrifugation to remove the unreacted feedstock. In most cases the unreacted anthracene will separate out with the adduct. In an alternative embodiment, the adduct and unreacted anthracene is separated from the reaction mixture by first cooling and filtering the reaction mixture to produce a solid adduct plus anthracene and a filtrate which contains a small amount of dissolved adduct and anthracene and subsequently flash distilling the filtrate to strip off the volatiles and leave a syrupy liquid containing a concentrated amount of adduct and anthracene. The recovered solids and syrupy liquid are suitably combined for pyrolysis.

The next step of the instant process is to heat or pyrolyze the recovered styrene-anthracene adduct at a temperature of from about 250 to about 450° C., preferably from about 300 to about 400° C. This pyrolysis frees the styrene from the anthracene, producing a mixture containing anthracene, styrene and any other olefins present in the feedstock. The anthracene is then separated from the styrene by conventional means, e.g., flash distillation, filtration, centrifugation, etc.

In an preferred embodiment, the adduct-forming reaction is carried out under a temperature and pressure maintained to keep the feedstock, anthracene and adduct in the liquid state. After adduction, xylene, ethylbenzene, unreacted styrene and similar volatiles are flashed off leaving molten anthracene and styrene-anthracene adduct. The remaining liquid mixture is then heated to pyrolyze the styrene-anthracene adduct and distill off the styrene. The remaining molten anthracene from this pyrolysis is cooled and recycled as a liquid back to the adduction reaction.

In the event that the feedstock also contained other olefins, they will also form adducts with the anthracene which will be separated from the anthracene during the pyrolysis step. The olefins can be separated from the styrene utilizing conventional techniques such as, for example, flashing, distillation, solvent extraction, moving bed adsorption and the like.

In certain instances polymerization of the styrene in the system to form polystyrene could be a problem, in which case polymerization inhibitors can be added to the instant process. These inhibitors are well known and include such examples as 4-tert-butyl catechol and 2,6-ditertbutyl para-cresol.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The present invention will now be illustrated by means of the following illustrative embodiments and examples which are provided for illustration and are not to be construed as limiting the invention.

EXAMPLES

The following example illustrates the process the instant invention.

A 100 ml Parr autoclave was charged with 35.6g(0.2 moles) of (unsubstituted) anthracene (Aldrich), 0.22 g (1 mmole) of 2,6-ditert-butyl para-cresol and 18.5 ml (15.8 g) of a hydrocarbon feedstock comprising by weight: 33% styrene (0.05 moles), 14% ethylbenzene, 44% mixed xylenes, 8% 1 octene and 1% n-octene. The reactor was purged three times with argon, sealed, placed in a heating bath and heated to 226-227° C. for 4 hours. The autoclave was stirred at 600 rpm during heating. The autoclave was then cooled to 20° C. The reaction mixture was diluted with 150 ml of n-pentane, filtered and the solids washed with an additional 50 ml of n-pentane. The combined filtrates [118g(A)]contained 0.72 g of unreacted styrene by gas chromatographic analysis. The solids were dried to give 29.4 g(B). Solution (A) was stripped at 150° C. at 1mm Hg to remove solvent and unreacted styrene (J) to leave 12.0 g of yellow syrup (C). Fractions (B) and (C) were combined to give 41.4 g of material which was pyrolyzed by heating at 270-380° C. at atmospheric pressure under a slow stream of nitrogen to give a colorless distillate (bp. 110-130° C.). The distillation column was washed with a small amount of pentane and collected in the distillation flask to give a pentane solution of the distillate [8.0g(F)], which was shown to contain 3.56 g of styrene by gas chromatographic analysis. The solid residue [59.4g]from the pyrolysis (G) was washed with pentane, filtered and dried to give 35.6 g (H) of recovered anthracene. Residue (G) which contained 0.06 g of styrene as determined by gas chromatographic analysis, was stripped at 80° C. under vacuum to give 1.5 g (I) of a mixture of unknown composition.

Gas chromatographic analysis showed: 86.2% conversion of styrene based on unreacted styrene contained in fraction (A); 83.5% total recovery of styrene based on styrene contained in fractions (A), (F) and (G); and 94.4% total recovery of 1-octene based on octene contained in fractions (A) and (F).

Additional experiments were carried out using differing anthracene/styrene ratios. These results of these experiments are shown in Table A. Additional experiments were carried out using substituted anthracenes. These results are shown in Table B.

TABLE A

| Expt. No. | Anthracene | Feed Stock Content, Moles Styrene | Feed Stock Content, Moles 1-Octene | Adduct Rxn. Time Hrs. | Pyrolysis Temp. °C. | Styrene Conv. % | Styrene Recovered[b] % | 1-Octene Recovered % |
|---|---|---|---|---|---|---|---|---|
| A-1 | 0.2 | 0.05 | 0.01 | 4 | 325–380 | 86.2 | 83.5 | 94.4 |
| A-2 | 0.2 | 0.05 | 0.01 | 2 | 325–380 | 86.3 | 78.3 | 100 |
| A-3 | 0.2 | 0.05 | 0.01 | 1 | 325–380 | 84.8 | 86.9 | 100 |
| A-4 | 0.15 | 0.05 | 0.01 | 4 | 325–380 | 85.2 | 76.0 | 95.2 |
| A-5 | 0.15 | 0.05 | 0.01 | 1 | 325–380 | 88.1 | 72.1 | 84.8 |
| A-6 | 0.10 | 0.05 | 0.01 | 1 | 325–380 | 85.2 | 69.0 | 90.4 |
| A-7[a] | 0.15 | 0.037 | — | 4 | 325–380 | 86.9 | 68.1 | — |

[a]Plant feed containing 11.3 wt % styrene.
[b]Material Balance includes unreacted styrene as well as styrene isolated via adduct pyrolysis.
ANTHRACENE: 0.2 mole = 35.6 g; 0.15 mole = 26.7 g; 0.10 mole = 17.8 g.
STYRENE: 0.10 mole = 10.4 g; 0.05 mole = 5.2 g; 0.037 mole = 3.83 g.
OCTENE: 0.02 mole = 2.50 g; 0.01 mole = 1.25 g.

TABLE B

| Expt. No. | Anthracene | Feed Stock Content, Moles Styrene | Feed Stock Content, Moles 1-Octene | Adduct Rxn. Time Hrs. | Pyrolysis Temp. °C. | Styrene Conv. % | Styrene Recovered[b] % | 1-Octene Recovered % |
|---|---|---|---|---|---|---|---|---|
| B-1 | 9,10-Dichloro- 0.15 | 0.05 | 0.01 | 1 | 325–380 | 97.3 | 79.8 | 80.8 |
| B-2 | 9-Methyl- 0.15 | 0.05 | 0.01 | 1 | 325–380 | 92.7 | 54.0 | 90.4 |

ANTHRACENE: 0.2 mole = 35.6 g; 0.15 mole = 26.7 g; 0.10 mole = 17.8 g.
STYRENE: 0.10 mole = 10.4 g; 0.05 mole = 5.2 g; 0.037 mole = 3.83 g.
OCTENE: 0.02 mole = 2.50 g; 0.01 mole = 1.25 g.

I claim:

1. A process for extracting styrene from a styrene-containing feedstock which comprises:
   (a) reacting said feedstock with an anthracene at a temperature ranging from about 175 to about 275° C. to form a styrene adduct with anthracene,
   (b) separating said adduct from the feedstock,
   (c) heating said separated adduct at a temperature of from between about 250 to about 450° C. to produce a mixture comprising anthracene and styrene, and
   (d) individually separating styrene and anthracene from the mixture formed in step (c).

2. The process of claim 1 wherein step (a) is carried out at a temperature from about 200 to about 250° C.

3. The process of claim 2 wherein step (a) is carried out at a temperature from about 210 to about 240° C.

4. The process of claim 2 wherein step (c) is carried out at a temperature of from about 300 to about 400° C.

5. The process of claim 3 wherein step (c) is carried out at a temperature of from about 325 to about 380° C.

6. The process of any one of claims 1 to 5 wherein the separations carried out in steps (b) and (d) are carried out by distillation.

7. The process of any one of claims 1 to 5 wherein the separations carried out in steps (b) and (d) are carried out by first cooling to cause precipitation, followed by filtration or centrifugation.

8. The process of any one of claims 1 to 5 wherein the feedstock additionally comprises ethylbenzene, xylenes and mixtures thereof.

9. The process of any one of claims 1 to 5 wherein the feedstock additionally comprises olefins which are extracted concurrently with the styrene and which are subsequently separated from the styrene.

10. The process of claim 9 wherein the olefin is an alpha olefin.

11. The process of any of claims 1 to 5 wherein the feedstock originates in an olefins pyrolysis unit.

* * * * *